United States Patent
Henry et al.

(10) Patent No.: US 9,636,115 B2
(45) Date of Patent: May 2, 2017

(54) VASO-OCCLUSIVE DELIVERY DEVICE WITH KINK RESISTANT, FLEXIBLE DISTAL END

(75) Inventors: William S. Henry, Oakland, CA (US); Charles Daly, Kanturk (IE); Russell Ford, Watsonville, CA (US); Michael D. Williams, Oakland, CA (US); Hanh Duong, Hayward, CA (US); Hughie Devaney, Skreen (IE); Kamal Ramzipoor, Fremont, CA (US); Clifford Teoh, Los Altos, CA (US); Richard Murphy, Sunnyvale, CA (US); Andrew Huffmaster, Newark, CA (US); Scott McGill, San Ramon, CA (US)

(73) Assignees: Stryker Corporation, Kalamazoo, MI (US); Stryker European Holdings I, LLC, Kalamazoo, MI (US)

( * ) Notice: Subject to any disclaimer, the term of this patent is extended or adjusted under 35 U.S.C. 154(b) by 2420 days.

(21) Appl. No.: 11/423,934

(22) Filed: Jun. 13, 2006

(65) Prior Publication Data
US 2007/0055302 A1    Mar. 8, 2007

Related U.S. Application Data

(60) Provisional application No. 60/690,570, filed on Jun. 14, 2005.

(51) Int. Cl.
*A61M 29/00* (2006.01)
*A61B 17/12* (2006.01)
*A61M 25/09* (2006.01)

(52) U.S. Cl.
CPC .. *A61B 17/12022* (2013.01); *A61B 17/12154* (2013.01); *A61B 17/12109* (2013.01);
(Continued)

(58) Field of Classification Search
CPC ........ A61B 17/12022; A61B 17/12154; A61B 2017/1205; A61B 2017/12054;
(Continued)

(56) References Cited

U.S. PATENT DOCUMENTS

| | | |
|---|---|---|
| 4,994,069 A | 2/1991 | Ritchart et al. |
| 5,122,136 A | 6/1992 | Guglielmi et al. |

(Continued)

OTHER PUBLICATIONS

PCT International Search Report for PCT/US2006/023443, Applicant Boston Scientific Scimed, Inc., forms PCT/ISA/210 and 220, dated Oct. 10, 2006 (6 pages).

(Continued)

*Primary Examiner* — Diane Yabut
(74) *Attorney, Agent, or Firm* — Vista IP Law Group, LLP

(57) ABSTRACT

A device for delivering an occlusive element includes an elongate sheath having a lumen therein. An elongate core member is disposed within the lumen and is formed from a proximal portion and distal portion connected via a joint. The distal portion of the elongate member includes a severable junction secured to the occlusive element. A marker coil is coaxially arranged around the distal portion of the elongate core member and is partially disposed inside the sheath lumen. A coil member is coaxially arranged around the distal portion of the elongate core member and coaxially arranged around at least a portion of the marker coil extending outside the lumen of the sheath. The coil member is secured at a distal end thereof to the distal portion of the elongate core member. The device resists axial compression while allowing for radial bending.

19 Claims, 4 Drawing Sheets

(52) U.S. Cl.
CPC . *A61B 17/12113* (2013.01); *A61B 2017/1205* (2013.01); *A61B 2017/12054* (2013.01); *A61B 2017/12063* (2013.01); *A61M 25/09* (2013.01); *A61M 2025/09133* (2013.01)

(58) Field of Classification Search
CPC A61B 2017/12063; A61B 2017/12109; A61B 2017/12113; A61M 25/09; A61M 2025/09133
USPC .......................................... 606/200; 600/585
See application file for complete search history.

(56) References Cited

U.S. PATENT DOCUMENTS

| | | |
|---|---|---|
| 5,226,911 A | 7/1993 | Chee et al. |
| 5,234,437 A | 8/1993 | Sepetka |
| 5,250,071 A | 10/1993 | Palermo |
| 5,261,916 A | 11/1993 | Engelson |
| 5,304,194 A | 4/1994 | Chee et al. |
| 5,304,195 A | 4/1994 | Twyford, Jr. et al. |
| 5,312,415 A | 5/1994 | Palermo |
| 5,350,397 A | 9/1994 | Palermo et al. |
| 5,354,295 A | 10/1994 | Guglielmi et al. |
| 5,382,259 A | 1/1995 | Phelps |
| 5,549,624 A | 8/1996 | Mirigian et al. |
| 5,690,666 A | 11/1997 | Berenstein et al. |
| 5,853,418 A | 12/1998 | Ken et al. |
| 5,941,888 A | 8/1999 | Wallace et al. |
| 6,123,714 A | 9/2000 | Gia et al. |
| 6,280,457 B1 | 8/2001 | Wallace et al. |
| 6,468,266 B1 * | 10/2002 | Bashiri et al. .................... 606/1 |
| 6,743,251 B1 | 6/2004 | Eder |
| 2001/0044633 A1 | 11/2001 | Klint |
| 2004/0002733 A1 | 1/2004 | Teoh |
| 2004/0034363 A1 | 2/2004 | Wilson et al. |
| 2004/0034378 A1 * | 2/2004 | Monstadt et al. ............ 606/157 |
| 2004/0078050 A1 | 4/2004 | Monstadt et al. |
| 2004/0167441 A1 * | 8/2004 | Reynolds et al. ............ 600/585 |
| 2004/0199175 A1 | 10/2004 | Jaeger et al. |
| 2004/0236344 A1 | 11/2004 | Monstadt et al. |
| 2005/0043755 A1 | 2/2005 | Wilson et al. |
| 2005/0061329 A1 | 3/2005 | Tran et al. |

OTHER PUBLICATIONS

PCT Written Opinion of the International Searching Authority for PCT/US2006/023443, Applicant Boston Scientific Scimed, Inc., Form PCT/ISA/237, dated Oct. 10, 2006 ( 5 pages).

* cited by examiner

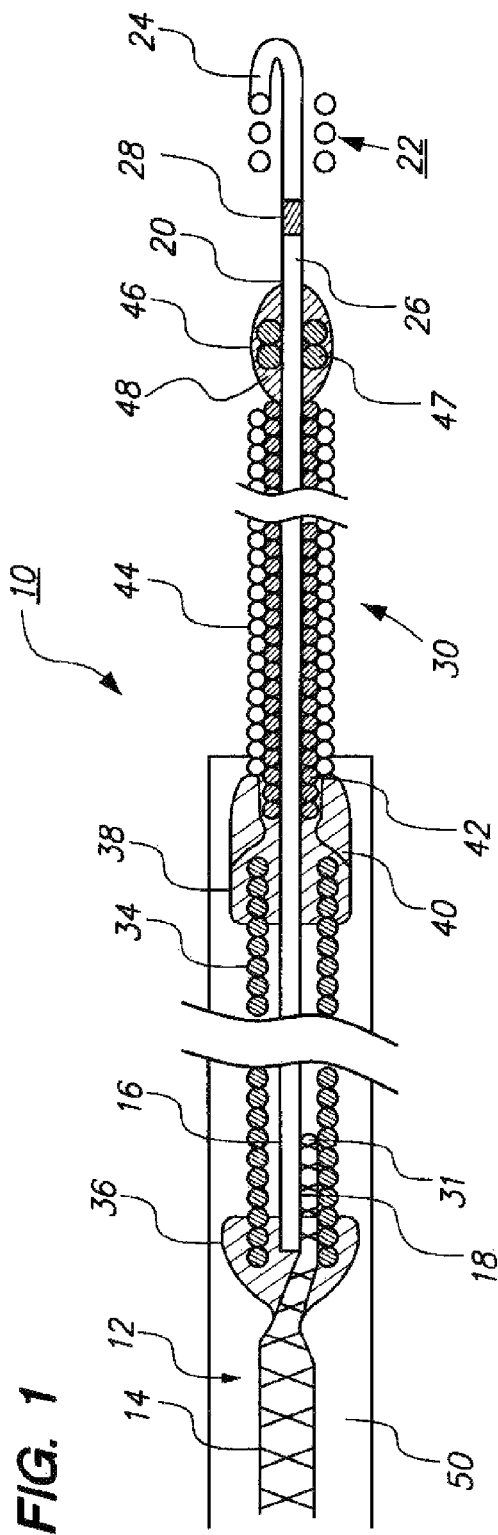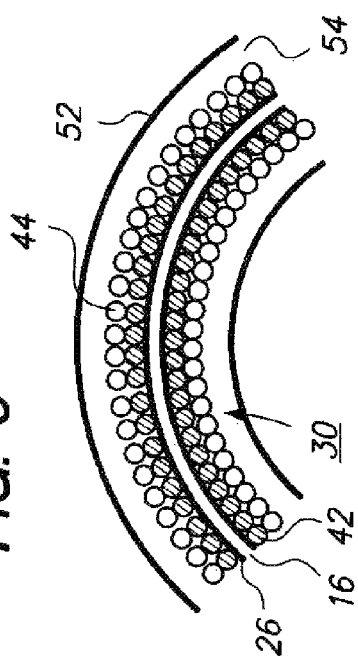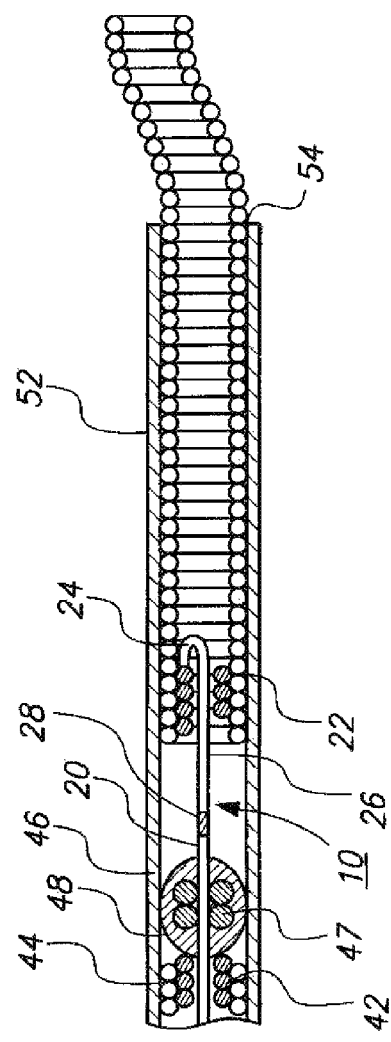

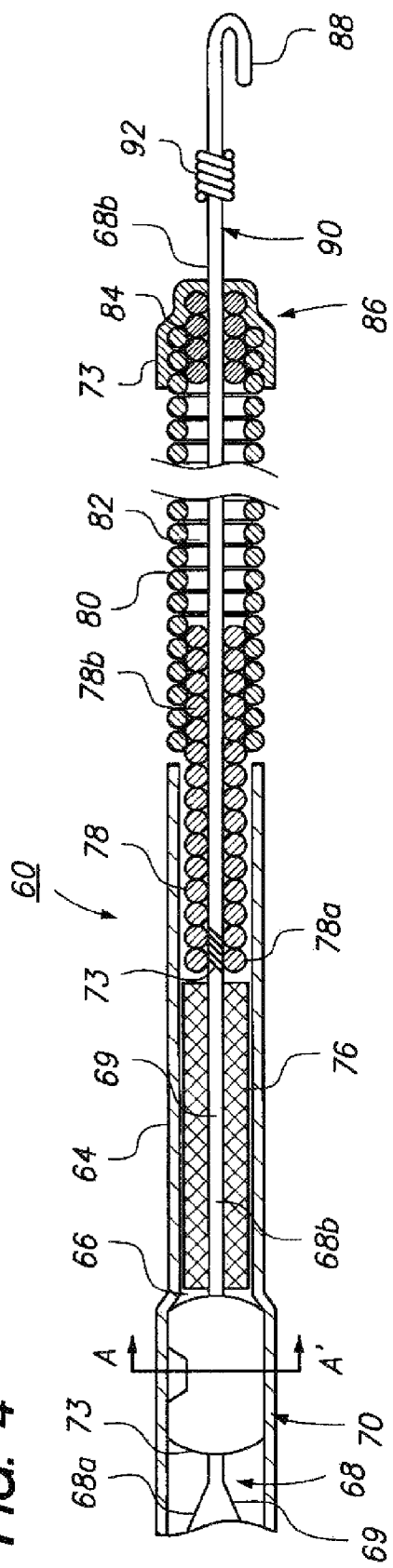
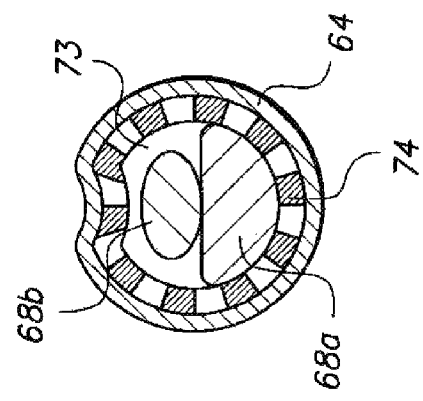
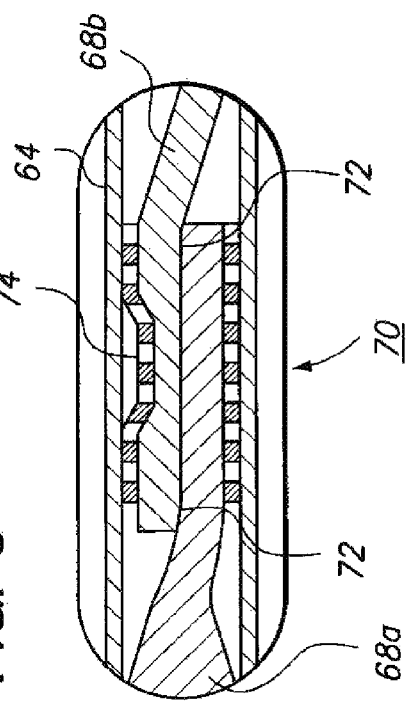
FIG. 4
FIG. 6
FIG. 5

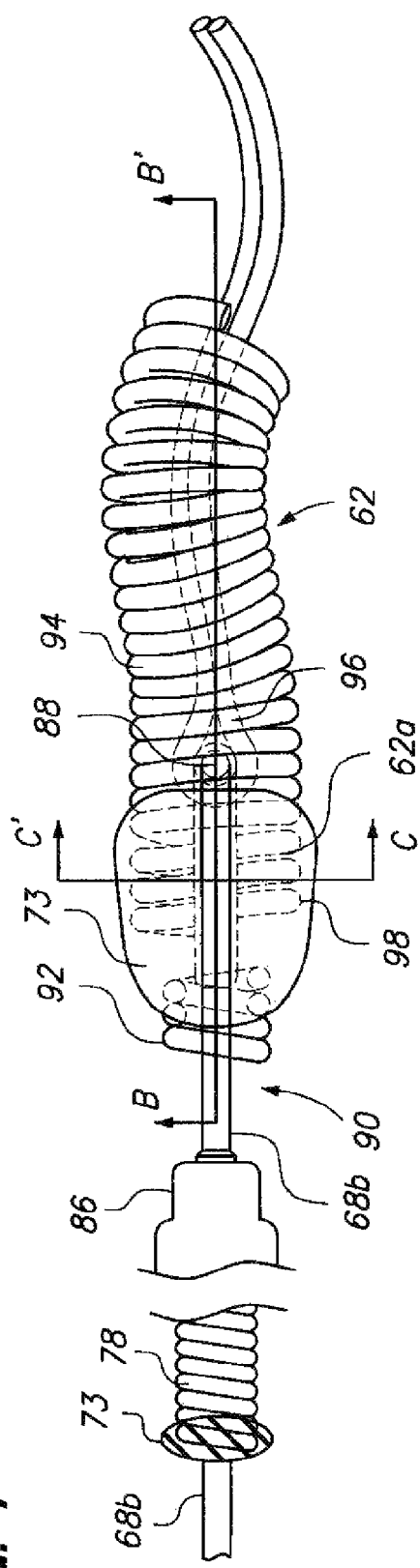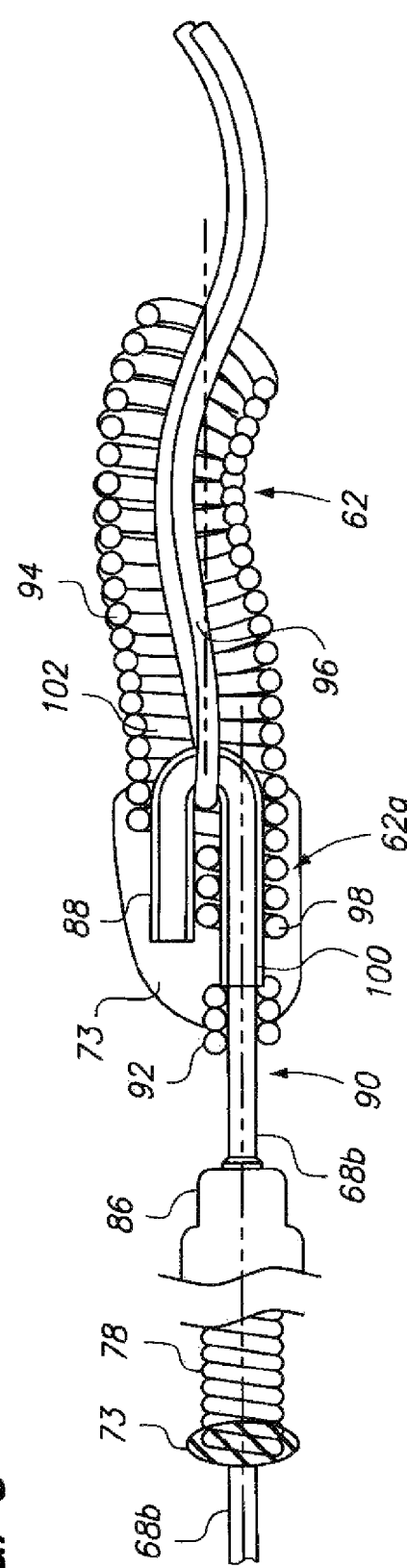

VASO-OCCLUSIVE DELIVERY DEVICE WITH KINK RESISTANT, FLEXIBLE DISTAL END

REFERENCE TO RELATED APPLICATIONS

This Application claims the benefit of U.S. Provisional Patent Application No. 60/690,570 filed on Jun. 14, 2005. U.S. Provisional Patent Application No. 60/682,562 is incorporated by reference as if set forth fully herein.

FIELD OF THE INVENTION

The field of the invention generally relates to systems and delivery devices for implanting vaso-occlusive devices for establishing an embolus or vascular occlusion in a vessel of a human or veterinary patient.

BACKGROUND OF THE INVENTION

Vaso-occlusive devices or implants are used for a wide variety of reasons, including treatment of intra-vascular aneurysms. A common vaso-occlusive device takes the form of a soft, helically wound coil formed by winding a platinum (or platinum alloy) wire strand about a primary mandrel. The relative stiffness of the coil will depend, among other things, on its composition, the diameter of the wire strand, the diameter of the primary mandrel, and the pitch of the primary windings. The coil is then wrapped around a larger, secondary mandrel, and again heat treated to impart a secondary shape. For example, U.S. Pat. No. 4,994,069, to Ritchart et al., describes a vaso-occlusive coil that assumes a linear, helical primary shape when stretched for placement through the lumen of a delivery catheter, and a folded, convoluted secondary shape when released from the delivery catheter and deposited in the vasculature.

In order to deliver the vaso-occlusive coils to a desired site, e.g., an aneurysm, in the vasculature, it is well-known to first position a small profile, micro-catheter at the site using a steerable guidewire. Typically, the distal end of the micro-catheter is provided, either by the attending physician or by the manufacturer, with a selected pre-shaped bend, e.g., 45°, 90°, "J", "S", or other bending shape, depending on the particular anatomy of the patient, so that it will stay in a desired position for releasing one or more vaso-occlusive coil(s) into the aneurysm once the guidewire is withdrawn. A delivery or "pusher" wire is then passed through the micro-catheter, until a vaso-occlusive coil coupled to a distal end of the pusher wire is extended out of the distal end opening of the micro-catheter and into the aneurysm. The vaso-occlusive device is then released or "detached" from the end pusher wire, and the pusher wire is withdrawn back through the catheter. Depending on the particular needs of the patient, another occlusive device may then be pushed through the catheter and released at the same site.

One known way to release a vaso-occlusive coil from the end of the pusher wire is through the use of an electrolytically severable junction, which is a small exposed section or detachment zone located along a distal end portion of the pusher wire. The detachment zone is typically made of stainless steel and is located just proximal of the vaso-occlusive device. An electrolytically severable junction is susceptible to electrolysis and, thus, disintegrates when the pusher wire is electrically charged in the presence of an ionic solution, such as blood or other bodily fluids. Thus, once the detachment zone exits out of the catheter distal end and is exposed in the vessel blood pool of the patient, a current applied to the conductive pusher wire completes a circuit with an electrode attached to the patient's skin, or with a conductive needle inserted through the skin at a remote site, and the detachment zone rapidly disintegrates due to electrolysis.

When the coil is being delivered, an axial force on the pusher member must be generated to overcome frictional forces with the micro-catheter and resistance to coil deployment into the aneurysm. In order to prevent columnar buckling due to this axial force, the distal end of the pusher wire proximal of the detachment zone is typically provided with a relatively stiff polymer jacket, e.g., made of polytetrafluoroethylene ("PTFE") and/or polyethyleneterephthalate ("PET"). While preventing axial compression, the stiff polymer jacket can change the distal bend shape of the delivery catheter and, thus, deflect the delivery catheter tip away from its desired position. For example, the stiff polymer jacket region may have a relatively long length (e.g., around 2 mm) which will inhibit the bending ability of the delivery device. The use of a stiff polymer jacket may also require the physician to relocate the catheter tip in the aneurysm during delivery of the occlusive device, or prior to placement of a further occlusive device, which undesirably extends the duration and risks of the procedure.

A relatively long pusher member junction can exacerbate the problem of conforming the vaso-occlusive coil and portion of the pusher member distal to the junction into the aneurysm. If these components do not fit in the aneurysm, the catheter can be pushed back and move out of position, which can leave a tail of the coil in the parent artery, or present difficulties in repositioning the micro-catheter for subsequent coils to be delivered. This is especially true in a tightly curved delivery catheter.

There thus is a need for an occlusive delivery system that retains good pushability while at the same time maintains good flexibility. For example, a delivery device is needed that includes a distal portion that is configured to resist axial compression while at the same time permitting radial bending.

SUMMARY

In one aspect of the invention, a device for delivering an occlusive element such as a vaso-occlusive coil includes an elongate sheath having a lumen therein. The device includes an elongate core member disposed within the lumen of the sheath. The elongate member is formed from a proximal portion and distal portion connected to one another via a joint. The distal portion of the elongate member includes a severable junction such as, for example, an electrolytically degradable junction that is secured to an occlusive element such as a vaso-occlusive coil. A marker coil is coaxially arranged around the distal portion of the elongate core member and is partially disposed inside the lumen of the sheath. A coil member is coaxially arranged around the distal portion of the elongate core member and coaxially arranged around at least a portion of the marker coil extending outside the lumen of the sheath. The coil member is secured at a distal end thereof to the distal portion of the elongate core member. The coil member may be secured to the elongate core member by a stopper coil. The device may utilize a hook to engage with a proximal end of the vaso-occlusive coil.

In another aspect of the invention, a device for delivering an occlusive element such as a vaso-occlusive coil includes an elongate sheath having a lumen therein. The device includes an elongate core member disposed within the lumen of the sheath. The elongate member is formed from a proximal portion and distal portion connected to one another via a joint. The distal portion of the elongate member includes a severable junction such as, for example, an electrolytically degradable junction that is secured to an occlusive element such as a vaso-occlusive coil. A spacer member is coaxially arranged around the distal portion of the elongate core member and is disposed inside the lumen of the sheath at a location distal with respect to the joint. A marker coil is coaxially arranged around the distal portion of the elongate core member and is disposed inside the lumen of the sheath at a location that is distal with respect to the spacer member. A coil member is coaxially arranged around the distal portion of the elongate core member and at least a portion of the marker coil. The coil member is secured at a distal end thereof to the distal portion of the elongate core member.

In certain embodiments of the invention, the core member includes a hook that is secured to one or more proximal windings of the vaso-occlusive coil. For example, the hook may be secured through one or more crimped windings on a proximal end of the coil. An adhesive or epoxy may aid is securely attaching the vaso-occlusive coil to the core member.

In another aspect of the invention, a method of loading a vaso-occlusive coil on a delivery device includes providing a delivery device that includes an elongate core member having a severable junction and a hook disposed at a distal end thereof. One or more proximal windings of the vaso-occlusive coil are crimped. The hook is inserted into a lumen of the crimped portion of the vaso-occlusive coil. The hook is then rotated about the long axis of the elongate core member and the elongate core member is retracted proximally to secure the hook to the vaso-occlusive coil. An adhesive or epoxy may be used to aid in securely attaching the vaso-occlusive coil to the core member.

In still another aspect of the invention a device for delivering a vaso-occlusive coil includes an elongate pusher member including a proximal portion joined to a distal portion at a joint. The distal portion includes a severable junction coupled to a vaso-occlusive coil. A marker coil is coaxially arranged around the elongate pusher member about the joint. A reinforcing member is coaxially arranged about the distal portion of the elongate pusher member distal with respect to the marker coil and proximal with respect to the severable junction, the reinforcing member including an inner coil and an outer coil.

BRIEF DESCRIPTION OF THE DRAWINGS

FIG. 1 illustrates a partial cross-sectional view of a distal end portion of a delivery device according to one embodiment.

FIG. 2 illustrates a partial cross-sectional view of the distal portion of the delivery device positioned within a delivery catheter. The delivery device is further shown connected to a vaso-occlusive coil.

FIG. 3 is a side, cross-sectional view illustrating the bending movement of the reinforcing member when subject to an axial force in a proximal direction.

FIG. 4 illustrates a partial cross-sectional view of distal end portion of a delivery device according to another embodiment of the invention.

FIG. 5 illustrates a magnified, cross-sectional view of the joint formed between the proximal core member and the distal core member.

FIG. 6 illustrates a cross-sectional view of the joint taken along the line A-A' in FIG. 4.

FIG. 7 illustrates a partial cross-sectional view of a distal end portion of the delivery device of FIG. 4 shown secured to a vaso-occlusive coil.

FIG. 8 illustrates a cross-sectional view of the distal end portion of the delivery device taken along the line B-B' in FIG. 7.

DETAILED DESCRIPTION OF THE ILLUSTRATED EMBODIMENTS

Figure 9:
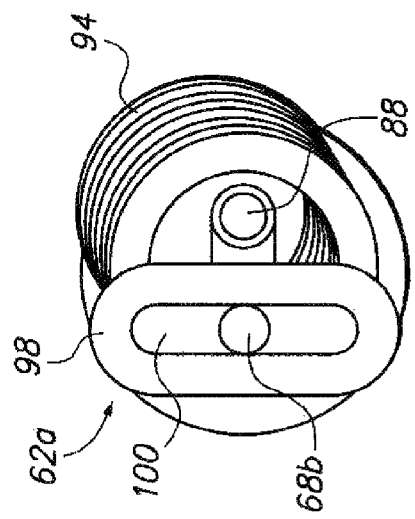
FIG. 9 illustrates a cross-sectional view of the distal end portion of the delivery device taken along the line C-C' in FIG. 7.

FIG. 1 illustrates an exemplary delivery system 10 according to one embodiment for the delivery of a vaso-occlusive device (not shown) to a vascular site in a human or veterinary patient includes an elongate pusher member 12 of conventional design and composition, except that, rather than comprising a unitary (single) wire member having a tapered distal end section, the pusher member 12 comprises a two-piece assembly, including a proximal pusher member 14 attached to a (lower profile) distal pusher member 16 at an attachment joint 18. It is believed that certain manufacturing advantages may be achieved by using a "two-piece" pusher member assembly, instead of a conventional unitary wire member. In particular, it is believed that the electrolytic detachment process may be more repeatable, and that manufacture of more uniform and consistent distal end dimensions may be achieved in a process using drawn wires having relatively small cross-sections that are attached to the main wire, rather than grinding down the distal end portion of the (larger) proximal cross-section needed for adequate stiffness and control to "push" the vaso-occlusive devices through the various bends and curves of the delivery catheter. It should be appreciated, however, that a two-piece pusher member is not required, and that a conventional (i.e., tapered distal end) single wire member may be used in alternate embodiments.

The distal pusher member 16 includes a straight wire section 20 that extends from the attachment joint 18 and forms a loopback coil section 22 at its distal end, including a distal end loop 24 for coupling with a vaso-occlusive device (not shown), in a manner such as disclosed in U.S. patent application Ser. Nos. 11/140,690 and 11/140,691, the contents of which are incorporated by reference as set forth fully herein. For example, the distal end loop 24 can engage a stretch resistance filament or an eyelet coupling of a distally extending vaso-occlusive device, depending on the design of the occlusive device. By way of another example, the loopback coil section 22 can be interwound with a vaso-occlusive coil, with an additional adhesive or polymeric heat shrink tubing added as needed for reinforcement.

The cross-section of the distal pusher member 16 may be circular or rectangular, or may alternate from substantially circular to substantially rectangular, for example, along different portions of the loopback coil section 22. In one embodiment, the straight wire section 20 extends approximately 32 mm from its proximal end at the attachment joint 18 to the beginning of the loopback coil section 22. All exposed areas of the distal pusher wire member 16, including especially the loopback coil section 22, are coated with an electrically insulating material 26, such as polyimide, polyurethane, PET, parylene, pTFE or other fluoropolymers, except for a small exposed area having a length that is a value between approximately 0.002 to 0.015 inches, and in certain aspects between 0.004 to 0.007 inches in axial length that forms an electrolytic detachment zone or severable junction 28.

Still referring to FIG. 1, the severable junction 28 is located immediately adjacent, e.g., approximately 0.02 inches proximal from the loopback coil section 22. The insulative coating 26 is very thin, in order to provide additional pathways through the entire delivery assembly 10 for alternating current to flow when electrical power is applied to the pusher member 12, which provides for greater ease in differentiating between true detachment, versus possible occlusion of the severable junction 28 by a non electrochemically conductive material. In one embodiment, the thickness of the polyimide insulating material 26 on the loopback coil section 22 is extremely thin, and may be between about 0.00001 to about 0.002 inches, in order to provide a desired alternating current conduction to the surrounding electrolyte for better detachment detection. Further details regarding the use of electrolytically detachable joints are described in U.S. Pat. Nos. 5,354,295, 5,122,136, and 5,941,888, which are expressly incorporated by reference as if set forth fully herein.

It should be appreciated that it is not essential to use an electrolytic link as the severable junction 28, and, in alternate embodiments, the severable junction 28 may be of a different type, such as a thermally or mechanically detachable link, which are well known in the art. Various mechanical detachment mechanisms are described in U.S. Pat. Nos. 5,234,437, 5,250,071, 5,261,916, 5,304,195, 5,312,415, and 5,350,397, which are expressly incorporated herein by reference. An exemplary thermally severable junction using low-frequency energy is described in U.S. Pat. No. 6,743,251, the contents of which are expressly incorporated by reference herein.

A radially flexible, axial reinforcing member, generally designated by reference numeral 30, is carried on the distal pusher member 16 proximal to the severable junction 28. The reinforcing member 30 is configured to resist axial compression, while allowing for radial bending of the distal pusher member 16 in response to a proximally directed axial force imparted on the delivery assembly 10, e.g., when a vaso-occlusive device is detached from the severable junction 28. In the delivery assembly 10 illustrated in FIG. 1, the bendable reinforcing member 30 comprises overlapping reinforcing coils 42, 44 placed concentric with the straight wire section 20 of the distal pusher member 16. In particular, an inner reinforcing coil 42 forms a lumen through which the distal pusher member 16 extends, and an outer reinforcing coil 44 forms a lumen through which the inner coil 42 extends.

In one embodiment, the inner and outer coils 42, 44 are each made of nickel-titanium, with the inner coil 42 having a greater axial length than the outer coil 44. The respective inner and outer coils 42, 44 can be provided with a slightly open pitch (e.g., less than or equal to about 20% of the wire diameter open or separated), or a substantially closed pitch (e.g., with adjacent windings that are touching or nearly touching) in order to enhance the columnar strength for advancing the vaso-occlusive member through the delivery catheter. In one embodiment, the inner coil 42 has a substantially closed pitch in order to provide maximum resistance to axial compression, while the outer coil 44 has a slightly open pitch, e.g., equal to or less than about 20% in order to facilitate radial bending in response to a proximally directed axial force imparted on the delivery assembly 10. In yet another embodiment, the outer coil 44 has pitch in a range of between about 2% to about 5%.

The outer diameter of the outer coil 44 is slightly greater than that of the loopback coil section 22, thus minimizing the tendency of the loopback coil section 22 to catch on the tip of the delivery catheter upon retraction of the delivery assembly 10 into the catheter lumen. In one embodiment, the outer coil 44 is made from 0.002 inch nickel-titanium wire wound on a 0.007 inch mandrel. The outer coil 44 may then be heat set, removed from the mandrel, and placed over the inner coil 42. The inner coil 42 may be made from 0.0015 inch nickel-titanium wire wound on a 0.0035 inch mandrel. The inner coil is also heat set, removed from the mandrel and placed over the straight section of the distal pusher member 16 prior to formation of the attachment joint 18.

In alternate embodiments, the respective inner and outer reinforcing coils 42, 44 may comprise a different metal, a metal alloy, a polymer, or some combination thereof. For example, in one contemplated alternate embodiment, one or both of the reinforcing coils 42, 44 may be made of a Nylon®. In another contemplated embodiment, one or both of the reinforcing coils 42, 44 have an inner metal (e.g., stainless steel) core, with an outer jacket made of low durometer polyethylene, or an elastomeric polymer with a lubricous coating to reduce surface friction, thus building up the outer diameter without imparting stiffness. Other embodiments are contemplated in which a single, large diameter reinforcing coil is used in place of the inner and outer coils 42, 44.

Still referring to FIG. 1, a distal stopper 46 is attached (e.g., crimped or welded) to the distal pusher member 16 just proximal of the detachment zone 28. The outer profile of the distal stopper 46 matches, in order to retain, the outer reinforcing coil 44. In the illustrated assembly 10, the distal stopper 46 comprises a few turns of metallic coil 47 welded in position to the distal wire member 16, and covered with electrically insulating material, such as heat shrink (PET) tubing 48. For example, two turns of 0.003 inch diameter stainless steel wire can be resistance welded through the polyimide insulation layer 26 (or an exposed portion thereof) and onto the wire member 16. Alternatively, the stopper 46 can be constructed of heat shrink tubing, or with a short piece of cured adhesive, less than or equal to approximately 0.020 inches in length.

As seen in FIG. 1, a proximal stopping member 40 comprising one or more polymer insulation layers (e.g., PTFE) or an adhesive is formed around the distal pusher member 16 to secure the reinforcing member 30. For example, the proximal stopping member 40 may be formed around the first few windings of the inner reinforcing coil 42 to secure the respective reinforcing coils 42, 44 in place axially along the distal pusher member 16.

The attachment joint 18 may be formed by a solder weld, adhesive, or other conventional attachment means, whereby a proximal portion of the straight wire section 20 of the distal pusher member 16 is attached to a distal end portion 31 of the proximal pusher member 14. As part of the assembly process, it may be necessary to grind (i.e., taper) down the profile of the distal end portion 31 of the proximal pusher member 14 in order to have a more uniform outer diameter transition. It may also be needed to strip away the polyimide insulation 26 (or other insulative material) from the straight wire section 20 of the distal pusher member in order to improve the metal-to-metal wire bonding. Optionally, a section of filler wire (not shown) may be added to the attachment joint 18 in order to provide a more circular outer diameter cross-section, i.e., with the proximal pusher member 14, distal pusher member 16, and filler wire, respectively, roughly forming a "three-lobe" cross-sectional shape.

In the illustrated assembly 10 of FIG. 1, a radio-opaque marker coil 34, made of, e.g., platinum or a platinum alloy, is positioned over the attachment junction 18. The materials used in constructing the marker coil 34 may be any of a wide variety of radio-opaque materials, and may be formed from a biologically compatible material. Suitable metallic materials include the Platinum Group metals, especially platinum, rhodium, palladium, rhenium, as well as tungsten, gold, silver, tantalum, and alloys of these metals. For example, one suitable metallic material is a platinum/tungsten alloy, e.g., 8% tungsten and the remainder platinum. Certain polymers can also be used as a suitable material for the marker coil 34 by filling the polymer with radio-opaque material, such as powdered tantalum, powdered tungsten, bismuth oxide, barium sulfate, and the like. Suitable polymers include most biocompatible materials that may be made in fibers, including thermoplastics, e.g., polyesters, such as PET, especially Dacron®; polyamides, including Nylon®; polyolefins, such as polyethylene, polypropylene, polybutylene, their mixtures, alloys, block, and random copolymers; and fluoropolymers, e.g., PTFE.

Respective proximal and distal PET covers 36 and 38 are provided to help fix the position of the respective wires 14, 16, as well as the marker coil 34, prior to application of a heat-activated bonding process. The proximal stopping member 40 also acts to insulate the marker coil 34 from the inner and outer reinforcing coils 42, 44. The attachment joint 18 (e.g., weld or solder joint) can be made through the platinum marker coil 34, thus assuring proper alignment of the marker coil 34 with respect to the detachment zone 28. This feature will aid the physician when aligning the marker coil 34 with the marking(s) on the delivery catheter 52. An insulating layer or sheath 50 made from, for example, PTFE is used to encapsulate the attachment joint 18, as well as the proximal end of the reinforcing coils 42, 44.

Referring to FIG. 2, the delivery catheter 52 comprises a delivery lumen 54 through which the delivery assembly 10 is slidably disposed. The catheter 52 is composed of a suitable flexible and biocompatible material that allows it to be delivered through the vasculature and positioned with its distal end opening in a targeted aneurysm. The delivery assembly 10 has a sufficiently small cross-sectional profile that enables it to be advanced through the delivery catheter 52, and access the targeted vascular site.

Referring to FIG. 3, when the assembly 10 is subjected to an axially force, the inner coil 42 of the reinforcing member 30 retains a substantially closed pitch. This is particularly true on the inner half of the illustrated bend, with its the successive windings remaining closely packed to resist axially compression of the reinforcing member 30. In contrast, the pitch of the windings of the outer coil 44 open to some extent, particularly the windings located on the outer portion of the illustrated bend to provide for radial bending of the reinforcing member 30.

With reference now to FIGS. 4-10, an alternative embodiment of a delivery device 60 for delivering an occlusive element 62 such as a vaso-occlusive coil (shown in FIGS. 7-9) is illustrated. FIG. 4 illustrates a cross-sectional view of a distal end of the delivery device 60. The device includes an elongate sheath 64 having a lumen 66 therein. The elongate sheath 64 may be formed from a flexible yet lubricious material such as polytetrafluoroethylene (PTFE) or the like. An elongate core member 68 is disposed inside the lumen 66 of the elongate sheath 64. In one embodiment of the invention, as best seen in FIGS. 4-6, the elongate core member 68 is formed from a proximal portion 68a that is joined to a distal portion 68b at a joint 70.

With regard to the proximal portion 68a, the elongate sheath 64 may be integral with or formed as a coating on one or more portions of the proximal elongate core member 68a. The proximal portion 68a of the elongate core member 68 may have a length on the order of around 140 cm. Of course, other lengths shorter or longer than 140 cm may be used in accordance with the invention. The proximal portion of the core member 68a may be formed from a metallic wire such as, for example, stainless steel. The proximal core member 68a may be coated with an insulative coating 69 such as, for instance, polyimide. Of course, other insulative materials like polyurethane, PET, or parylene may also be used. Typically, the proximal end (not shown) of the proximal core member 68a may be exposed or uncoated such that an electrical connection can readily be made during severing of the main occlusive element 62.

As best seen in FIGS. 5 and 6, the proximal core member 68a is secured to the distal core member 68b at the joint 70. The joint 70 may be formed by one or more welds 72 formed between the proximal and distal core members 68a, 68b. In FIGS. 5 and 6, the joint 70 is formed within a stainless steel hypotube segment 74 (e.g., type 304 stainless steel). The hypotube 74 assists in aligning the proximal and distal core members 68a, 68b for welding. The welds 72 may be formed directly through the hypotube 74 using conventional resistance welding techniques. One or both of the proximal and distal core members 68a, 68b may need to have their exterior surfaces ablated of any insulative layer(s) prior to welding. An epoxy of adhesive 73 (best seen in FIG. 6) may also be used to aid in forming the joint 70. For example, the epoxy 73 may be a cyanoacrylate-based epoxy such as EPOTEK 353 ND available from Epoxy Technology, Billerica, Mass. Generally, the distal core member 68b may have a length on the order of 38 cm. Of course, the distal core member 68b may be shorter or longer than 38 cm.

The distal core member 68b may be formed from wire such as, for instance, type 304 stainless steel wire. The distal core member 68b may be coated (with the exception of the detachment region) with an insulative coating 69. The insulative coating 69 may include, for instance, a polyimide-based coating or other insulative materials discussed herein. Still referring to FIG. 4, a spacer member 76 is positioned coaxially around the distal core member 68b. The spacer member 76 is contained within the lumen 66 of the sheath 64 and may be formed from a polyimide extrusion. The spacer member 76 aids in preventing kinking of the device 60. Moreover, the spacer member 76 assists the pushability of the device 60.

With reference still to FIG. 4, a marker coil 78 is coaxially arranged around the distal core member 68b. The marker coil 78 is also at least partially contained within the lumen 66 of the sheath 64. As seen in FIG. 4, a proximal portion 78a of the marker coil 78 is contained within the sheath 64 while a distal portion 78b of the maker coil 78 extends beyond a distal end of the sheath 64. The maker coil 78 may be affixed to the distal core member 68b at a proximal end thereof using an epoxy or adhesive 73 (e.g., DYMAX). The marker coil 78 is made of a radiopaque material such as, for example, platinum wire. Because the marker coil 78 is made of a radiopaque material, it can be readily visualized during fluoroscopy procedures.

Continuing along in the distal direction of the device 60, a coil member 80 is coaxially arranged around the exterior surface of the marker coil 78. In this regard, a friction fit is formed between the coil member 80 and the marker coil 78. The assembly is formed by sliding the outer coil member 80 over the marker coil 78. The outer coil member 80 advantageously imparts kink resistance and pushability to the device 60. The outer coil member 80 has an outer diameter on the order of the outer diameter of the sheath 64. The outer coil member 80 may be made of wire such as, for example, stainless steel wire.

The distal end of the coil member 80 is secured to the distal core member 68 via an stopper coil 84. The stopper coil 84 is positioned coaxially around the distal core member 68b and within the central lumen 82 of the coil member 80. The stopper coil 84 may be formed from several turns of a wire such as, for instance, stainless steel wire. An epoxy or adhesive 73 (e.g., EPO-TEK 353 ND available from Epoxy Technology, Billerica, Mass. 01821) may be used over both the distal end of the coil member 80 and stopper coil 84 to form a distal stop 86.

As best seen in FIG. 4, the distal core member 68b continues distally beyond the distal stop 86 and terminates in a hook portion 88. A severable junction 90 is formed on the distal core member 68b in the region bounded by the distal stop 86 and the hook portion 88. The severable junction 90 is formed from a section or region of the distal core member 68b that does not contain an insulative coating 69. The insulative coating 69 may be ablated (or not formed) in this region such that it is exposed to physiological fluids (e.g., blood or the like) during deployment. An advantage of the current design is that the distal core member 68b in the severable junction 90 has a relatively small outer diameter (generally within the range of about 0.001" to about 0.0025". Because of this feature, there is less material that needs to dissolve upon application of electrical current. Consequently, the current device 60 has a reduced detachment time as compared to other devices that use thicker wires.

The distal core member 68b includes a small segment of coil 92 located distally with respect to the detachment zone 90. The coil 92 is primarily used as an aid in determining whether or not the occlusive element 62 has severed from the distal core member 68b. The coil 92 may be formed from several windings of a platinum/tungsten wire around the distal core member 68b.

With reference to FIGS. 7-9, the hook portion 88 of the distal core member 68b engages with one or more windings 94 of the vaso-occlusive coil 62. Optionally, the hook portion 88 may also engage with a stretch resistant member 96. For example, one end of the stretch resistant member 96 may be secured to the hook 88 while the remaining end of the stretch resistant member 96 is secured to a distal segment of the vaso-occlusive coil 62 (not shown). The stretch resistant member 96 may be of the type disclosed in U.S. Published Application No. 2004-0002733A1 (Ser. No. 10/185,671) which is incorporated by reference as if set forth fully herein. The stretch resistant member 96 may be formed from a polymeric material such as, for example, polypropylene.

As seen in FIGS. 8 and 9, a proximal end 62a of the vaso-occlusive coil 62 is crimped to form one or more crimped windings 98. The hook portion 88 of the distal core member 68b passes through a lumen 100 formed in the crimped windings 98 and returns via a lumen 102 in the un-crimped windings 94. As seen in FIGS. 7 and 8, epoxy, solder, or adhesive 73 (e.g., DYMAX) is formed over the proximal end 62a of the vaso-occlusive coil 62 to create a secure attachment point between the vaso-occlusive coil 62 and the distal core member 68b. As seen in FIGS. 7 and 8, the epoxy 73 may be overlaid over one or more of the proximal un-crimped windings 94, the crimped windings 98, and the small segment of coil 92.

The hook 88 is formed by bending the distal end of the distal core member 68b back upon itself. Tweezers, forming mandrels, or other similar tools may be used to form the hook portion 88. The proximal end 62a of the vaso-occlusive coil 62 is then crimped by the use of a crimping tool (not shown). If a stretch resistant member 96 is used, the stretch resistant member 96 is then threaded through the vaso-occlusive coil 62. Next, the hook portion 88 is then inserted into the lumen 100 formed in the crimped windings 98. After passing through the lumen 100, the hook portion 88 (or vaso-occlusive coil 62) is then rotated through approximately 90 degrees to align the hook 88 relative to the vaso-occlusive coil 62 as best shown in FIG. 9. The distal core member 68b is then retracted proximally (or the vaso-occlusive coil 62 moved distally) to form the hooked arrangement illustrated in FIGS. 7-9. The epoxy 73 can then be applied or overlaid over the hook portion 88 to form the secure attachment point.

Figure 10:
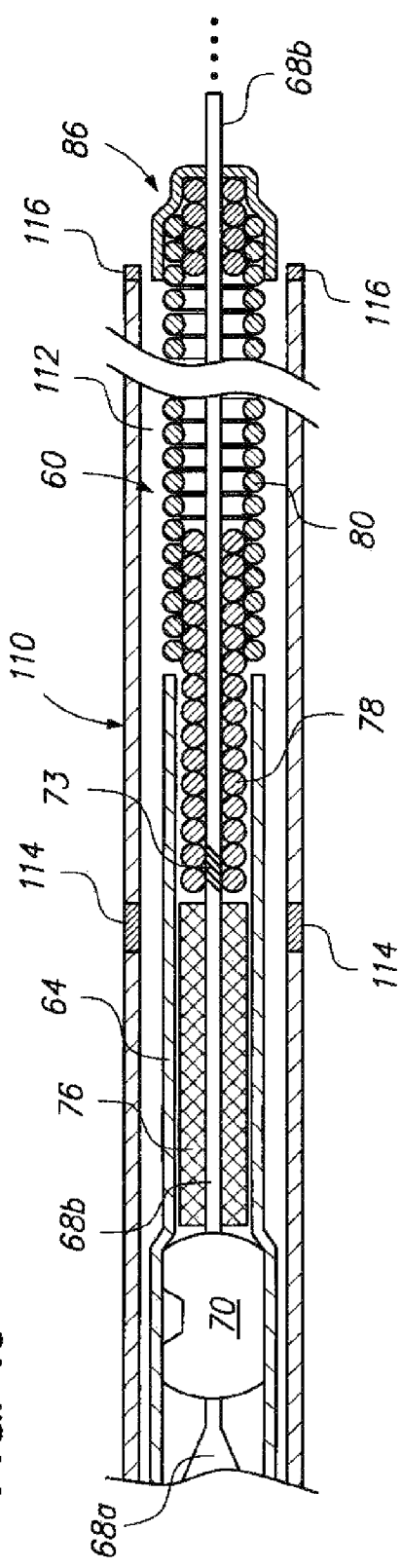
FIG. 10 illustrates a partial cross-sectional view of the delivery device of FIG. 4 positioned within a delivery catheter. The delivery catheter is aligned with respect to the delivery catheter via multiple radiopaque markers.

FIG. 10 illustrates the delivery device 60 positioned within a delivery catheter 110. The delivery device 60 is slidably along at least a portion of the length of the delivery catheter 110. The delivery catheter 110 (also referred to as a micro-catheter) is typically formed as a flexible, elongate member having a delivery lumen 112. Generally, the delivery device 60 may be used in connection with a delivery catheter 110 having an internal diameter within the range of about 0.016 inches to about 0.019 inches. FIG. 10 illustrates the alignment of the marker coil 78 just distally with respect to a first radiopaque marker 114 positioned on the delivery catheter 110. The radiopaque marker 114 may be formed as a ring or band about the periphery of the delivery catheter 110. A second radiopaque marker 116 is positioned at a distal end of the catheter 110 and may also be formed as a ring or band around the periphery of the delivery catheter 110. As seen in FIG. 10, the distal stop 86 projects just distally beyond the second radiopaque marker 116. The position of the delivery device 60 with respect to the delivery catheter 110 illustrated in FIG. 10 is the position of the delivery device 60 during deployment of the occlusive element 62. By aligning the marker coil 78 with the first and second radiopaque markers 114, 116 as shown in FIG. 10, the physician can be confident regarding the positioning of the occlusive element 62 for deployment.

When manufacturing the vaso-occlusive coil 62, the coil material is wound into a coil, which will typically be linear. Generally speaking, the coil 62 is a metallic coil made from a platinum alloy or a super-elastic alloy such as titanium/nickel alloy, known as "NITINOL". The diameter of the wire used in the production of the coils 62 may fall in the range of about 0.00025 inches to about 0.006 inches. The coil 62 may have a primary diameter of between about 0.003 and about 0.025 inches, but for most neurovascular applications, a diameter between about 0.008 to about 0.018 inches provides sufficient hoop strength to hold the coil 62 in place within the chosen body site, lumen, or cavity, without substantially distending the wall of the site and without moving from the site as a result of the repetitive fluid pulsing found in the vascular system.

The axial length of the coil wire will usually fall in the range of around 0.5 to around 100 cm, more usually around 2.0 to 40 cm. Depending upon usage, the coil 62 may well have 10-75 turns per millimeter or even 10-40 turns per millimeter. Of course, all of the dimensions provided above should be viewed only as guidelines, and the invention, in its broader aspects, should not be limited thereto. Dimensions that are suitable for use in occluding sites within the human body are included in the scope of this invention.

Depending on the desired therapeutic effect and the shape of the site to be treated, the coil 62 may later be treated or accessorized in numerous ways in order to enhance its therapeutic effect. The coil 62 may be made to form various secondary shapes, often through the use of heat treatment, that may be better suited to fill a particular treatment site, as disclosed in U.S. Pat. Nos. 5,853,418 and 6,280,457, the entireties of which are expressly incorporated herein by reference. Alternatively, the coil 62 may have little or no shape after introduction into the vascular space, as disclosed in U.S. Pat. No. 5,690,666, the entirety of which is expressly incorporated by reference herein. In addition, external materials may be added to the outside of the coil 62 in an effort to increase its thrombolytic properties. These alternative embodiments are disclosed in U.S. Pat. Nos. 5,226,911, 5,304,194, 5,549,624, 5,382,259, and 6,280,457, the entireties of which are expressly incorporated herein by reference.

One advantage of the delivery device 60 is that no PET sheath or tubing is needed to secure the occlusive element 62 to the distal core member 68*b*. Prior delivery devices have utilized a relatively long, stiff section of PET to secure a pusher wire to the vaso-occlusive element. These prior junctions are, however, typically long (e.g., 2 mm in length) and relatively stiff. In contrast, in the delivery device 60 described herein, the joint formed between the distal core member 68*b* and the occlusive element 62 is much shorter— between about 0.50 mm to about 0.75 mm in length. In addition, because no PET sheath/tubing is used, there is no need to apply heat.

During operation of the delivery device 60, electrical current is delivered to elongate core member 68. For example, a proximal end of the proximal core member 68*a* is coupled to a current source (not shown) that is located external to patient. Current may then be delivered via the core member 68, passing from the proximal portion 68*a* to the distal portion 68*b*. The portion of the core member 68*b* in the severable junction 90 then undergoes electrolytic degradation in the presence of a physiologic fluid such as blood. Electrolytic degradation continues until the occlusive element 62 is severed from the distal core member 68*b*. In order to form a complete circuit, a counter electrode (not shown) may also be used. For example, a counter electrode in the form of a patch or the like may be affixed to the patient's skin. The counter electrode may be formed from any suitable electrical conductor, for example, a conducting polymer, a conducting gel, or a metal, such as stainless steel, gold or platinum. Typically, at least a portion of the surface of the counter electrode is generally in contact with an electrolyte, in order to provide a return path for electrons.

While embodiments of the present invention have been shown and described, various modifications may be made without departing from the scope of the present invention. The invention, therefore, should not be limited, except to the following claims, and their equivalents.

What is claimed is:

1. A vaso-occlusive assembly, comprising:
   an elongate sheath having a wall and defining an axial lumen;
   respective proximal and distal elongate core members disposed within the lumen of the sheath, wherein the proximal elongate core member is joined to the distal elongate core member at a joint located within the sheath lumen, the distal elongate core member including a severable junction;
   a marker coil coaxially arranged around the distal elongate core member and partially disposed within the lumen of the sheath;
   a coil member coaxially arranged around the distal elongate core member and further coaxially arranged around at least a portion of the marker coil, the coil member further being secured at a distal end thereof to the distal elongate core member; and
   a vaso-occlusive coil coupled to the distal elongate core member at a location distal to the severable junction.

2. The assembly of claim 1, wherein the distal elongate core member includes a hook that is secured to one or more proximal windings of the vaso-occlusive coil.

3. The assembly of claim 2, wherein the interface between the hook and the one or more proximal windings of the vaso-occlusive coil is covered with an adhesive.

4. The assembly of claim 2, wherein the one or more proximal windings are crimped about a portion of the hook.

5. The assembly of claim 2, further comprising a stretch resistant filament secured at one end to the hook and at another end to the vaso-occlusive coil.

6. The assembly of claim 1, further comprising a delivery catheter defining an axial lumen, the vaso-occlusive assembly being slidable through the lumen of the delivery catheter.

7. The assembly of 1, wherein the coil member is secured to the distal elongate core member via a stopper coil and adhesive.

8. The assembly of claim 1, wherein the joint is contained within a segment of hypotube.

9. A vaso-occlusive assembly, comprising:
   an elongate sheath having a wall and defining an axial lumen therethrough;
   an elongate core member disposed within the lumen of the sheath, the elongate core member including a proximal portion joined to a distal portion at a joint, the distal portion including a severable junction;
   a spacer member coaxially arranged around the distal portion of the elongate core member and disposed within the lumen of the sheath at a location distal to the joint;
   a marker coil coaxially arranged around the distal portion of the elongate core member and disposed within the lumen of the sheath at a location distal to the spacer member;
   a coil member coaxially arranged around the distal portion of the elongate core member and at least a portion of the marker coil, the coil member further being secured at a distal end thereof to the distal portion of the elongate core member; and
   a vaso-occlusive coil coupled to the distal portion of the core member at a location distal to the severable junction.

10. The assembly of claim 9, wherein the coil member is secured to the distal portion of the elongate core member via a stopper coil and adhesive.

11. The assembly of claim 9, wherein the joint is contained within a segment of hypotube.

12. The assembly of claim 9, wherein the spacer member comprises a polyimide material.

13. The assembly of claim 9, wherein the distal portion of the core member in the region of the severable junction has a diameter within the range of about 0.001" to about 0.0025".

14. The assembly of claim 9, wherein the coil member comprises a stainless steel coil.

15. The assembly of claim 9, wherein the distal portion of the core member includes a hook that is secured to one or more proximal windings of the vaso-occlusive coil.

16. The assembly of claim 15, wherein the interface between the hook and the one or more proximal windings of the vaso-occlusive coil is covered with an adhesive.

17. The assembly of claim 15, wherein the one or more proximal windings are crimped about a portion of the hook.

18. The assembly of claim 15, further comprising a stretch resistant filament secured at one end to the hook and at another end to the vaso-occlusive coil.

19. The assembly of claim 15, further comprising a delivery catheter defining an axial lumen therethrough, the vaso-occlusive assembly being slidable through the lumen of the delivery catheter.

* * * * *